US010292898B2

(12) United States Patent
Amblard et al.

(10) Patent No.: US 10,292,898 B2
(45) Date of Patent: May 21, 2019

(54) DEVICE FOR OPTIMIZATION OF SLEEP APNEA SYNDROME THERAPY BY KINESTHETIC STIMULATION

(71) Applicants: SORIN CRM SAS, Clamart (FR); INSERM-INSTITUT DE LA RECHERCHE MÉDICALE, Paris (FR); UNIVERSITÉ JOSEPH FOURIER, Grenoble (FR); UNIVERSITÉ DE RENNES 1, Rennes (FR)

(72) Inventors: Amel Amblard, Sceaux (FR); Laurence Graindorge, Thouareé sur Loire (FR); Delphine Feuerstein, Issy les Moulineaux (FR); Alfredo Hernandez, Cesson Sévigné (FR); Jean-Louis Pépin, Grenoble (FR)

(73) Assignees: SORIN CRM SAS, Clamart (FR); INSERM-INSTITUT DE LA RECHERCHE MÉDICALE, Paris (FR); UNIVERSITÉ JOSEPH FOURIER, Grenoble (FR); UNIVERSITÉDE RENNES 1, Rennes (FR)

( * ) Notice: Subject to any disclaimer, the term of this patent is extended or adjusted under 35 U.S.C. 154(b) by 532 days.

(21) Appl. No.: 14/961,403

(22) Filed: Dec. 7, 2015

(65) Prior Publication Data
US 2016/0158093 A1    Jun. 9, 2016

(30) Foreign Application Priority Data
Dec. 8, 2014   (FR) ..................... 14 62054

(51) Int. Cl.
*A61B 5/00*    (2006.01)
*A61H 23/00*   (2006.01)
(Continued)

(52) U.S. Cl.
CPC ......... *A61H 23/004* (2013.01); *A61B 5/4818* (2013.01); *A61B 5/4836* (2013.01); (Continued)

(58) Field of Classification Search
CPC ................. A61H 23/004; A61H 23/02; A61H 2230/405; A61H 2230/207; (Continued)

(56) References Cited

U.S. PATENT DOCUMENTS 4,788,968 A * 12/1988 Rudashevsky ..... A61H 23/0218
310/30
5,277,694 A    1/1994 Leysieffer et al.
(Continued)

FOREIGN PATENT DOCUMENTS

EP    1 317 943 A1    6/2003
EP    1 319 421       6/2003
(Continued)

OTHER PUBLICATIONS

U.S. Appl. No. 14/961,348, filed Dec. 7, 2015, Amblard et al.
(Continued)

*Primary Examiner* — Steven O Douglas
(74) *Attorney, Agent, or Firm* — Foley & Lardner LLP (57) ABSTRACT

A device includes a processor configured to detect a respiratory disorder episode and generate kinesthetic stimulation control signals in response to the detection of a respiratory disorder episode. The device further includes at least one kinesthetic effector adapted to be applied to a patient's outer skin site and includes a vibrating electromechanical transducer capable of receiving stimulation control signals and outputting a kinesthetic stimulation energy determined by the stimulation control signals. The processor is further configured to determine the effectiveness of stimulation by detecting a cessation of the respiratory disorder episode. The
(Continued)

processor is further configured to determine a stimulation energy by selecting an initial energy value and varying the energy value as a function of the effectiveness of previous stimulation.

12 Claims, 4 Drawing Sheets

(51) Int. Cl.
| | |
|---|---|
| *G06F 19/00* | (2018.01) |
| *A61H 23/02* | (2006.01) |
| *A61B 5/04* | (2006.01) |
| *A61B 5/08* | (2006.01) |
| *A61H 39/00* | (2006.01) |
| *A61N 1/36* | (2006.01) |
| *A61M 21/00* | (2006.01) |
| *A61M 21/02* | (2006.01) |

(52) U.S. Cl.
CPC ........ *A61H 23/02* (2013.01); *G06F 19/3481* (2013.01); *A61B 5/04* (2013.01); *A61B 5/08* (2013.01); *A61H 39/007* (2013.01); *A61H 2201/10* (2013.01); *A61H 2201/5007* (2013.01); *A61H 2201/5012* (2013.01); *A61H 2205/027* (2013.01); *A61M 21/02* (2013.01); *A61M 2021/0022* (2013.01); *A61M 2205/505* (2013.01); *A61M 2230/06* (2013.01); *A61M 2230/205* (2013.01); *A61M 2230/42* (2013.01); *A61N 1/36* (2013.01)

(58) Field of Classification Search
CPC ...... A61H 2230/065; A61H 2201/5058; A61H 2201/5015; A61H 39/002; A61H 2201/0157; A61H 2203/0456; A61H 2205/027; A61H 2230/04; A61H 2230/045; A61H 39/07; A61H 2201/10; A61H 2201/2007; A61H 2201/5012; A61B 5/4818; A61B 5/4836; A61B 5/04; A61B 5/08; A61N 1/3611; A61N 1/36; G06F 19/3481
See application file for complete search history.

(56) References Cited

U.S. PATENT DOCUMENTS

| | | |
|---|---|---|
| 5,555,891 A | 9/1996 | Eisenfeld |
| 2007/0032733 A1 | 2/2007 | Burton |
| 2007/0208269 A1* | 9/2007 | Mumford ............. A61B 5/0002 600/546 |
| 2008/0009915 A1 | 1/2008 | Moses et al. |
| 2008/0033304 A1* | 2/2008 | Dalal .................. A61B 5/0205 600/484 |
| 2008/0154330 A1 | 6/2008 | Tehrani et al. |
| 2009/0192556 A1* | 7/2009 | Wu ...................... A61B 5/0031 607/3 |
| 2010/0048985 A1 | 2/2010 | Henke et al. |
| 2010/0087701 A1* | 4/2010 | Berka .................. A61M 21/02 600/27 |
| 2012/0089199 A1* | 4/2012 | Bolea .................. A61N 1/0556 607/42 |
| 2013/0144152 A1 | 6/2013 | Cervantes |
| 2014/0051938 A1 | 2/2014 | Goldstein et al. |
| 2014/0088378 A1* | 3/2014 | Muzet ................ A61B 5/02125 600/301 |

FOREIGN PATENT DOCUMENTS

| | | |
|---|---|---|
| EP | 2 313 151 | 4/2011 |
| WO | WO-96/28093 | 9/1996 |
| WO | WO-2007/141345 | 12/2007 |
| WO | WO-2009/154458 | 12/2009 |

OTHER PUBLICATIONS

U.S. Appl. No. 14/961,379, filed Dec. 7, 2015, Amblard et al.
Preliminary Search Report for French Patent Application No. 1462039, dated Jul. 28, 2015, 2 pages.
Preliminary Search Report for French Patent Application No. 1462041, dated Jul. 28, 2015, 2 pages.
Preliminary Search Report for French Patent Application No. 1462054, dated Apr. 8, 2015, 2 pages.

* cited by examiner

DEVICE FOR OPTIMIZATION OF SLEEP APNEA SYNDROME THERAPY BY KINESTHETIC STIMULATION

CROSS-REFERENCE TO RELATED PATENT APPLICATIONS

This application claims the benefit of and priority to French Patent Application No. 1462054, filed Dec. 8, 2014, which is incorporated herein by reference in its entirety.

BACKGROUND

The disclosure relates to the diagnosis and therapy of sleep disorders.

More particularly, the disclosure relates to a "kinesthetic stimulation" device which is a device for external sensory stimulation of the patient by a vibrator in contact with the skin in a sensitive and precise region of the body of the patient. Activating this vibrator has the effect of locally exciting cutaneous or mechanoreceptor endings of the skin, and triggering a response from the patient's autonomic nervous system, with sympathetic predominance (hereinafter "autonomic response").

The autonomic response to sympathetic activation is observable on the major modulator effects of cardiac activity, for example a chronotropic effect (e.g., a heart rate increase, a decrease in RR intervals, etc.) and an inotropic effect (e.g., heart contractility increase, etc.). This autonomic response is also observable on the peripheral vasoconstriction, which is increased during sympathetic autonomic activation.

In addition to these effects on cardiac activity, a sympathetic activation causes responses in the respiratory system and/or in the central nervous system (autonomic awakenings).

Such a noninvasive technique acts on a number of sleep disorders in alternative ways to the conventional therapeutic approaches that are based on the application of a continuous positive airway pressure through a face mask (a therapy by CPAP), the use of a mandibular orthosis and/or electrical stimulation of the hypoglossal nerve, which involves the implantation of a pacemaker.

In particular, the respiratory disease known as "sleep apnea syndrome" (SAS) is characterized by the frequent occurrence (at least 10 to 20 times per hour) of apneas during a patient's sleep phase, an "apnea" (or respiratory pause) being defined as a temporary cessation of breathing for a duration longer than 10 s. SAS can also be characterized by the occurrence of hypopnea under the same conditions, a "hypopnea" being defined as a significant decrease (without interruption) of the breathing rate, typically a decrease of more than 50% compared to a previous reference average value.

This pathology reaches more than 4% of the population and more than 50% of patients with heart failure. To protect the individual against asphyxiation due to the decrease in blood oxygen concentration during the interruption or the reduction of respiratory rate, the body adapts itself but with a deleterious effect on sleep, causing unconscious micro-arousals. The consequence is daytime sleepiness in the wakeful stage, with loss of attention and increased risk of accident. Furthermore, several studies have shown a higher incidence of blood disorders such as hypertension, ventricular arrhythmias, myocardial infarction and heart failure in patients with SAS.

Several documents describe the ability to stop apnea episodes through a stimulation therapy. For example, U.S. Pat. No. 5,555,891 A describes a vibrotactile stimulation system to stop apnea in newborns. The objective is to provide a system capable of detecting apnea and of stimulating the child to stop apnea, with stimulation energy that may vary to avoid habituation. The applied energy is important and often involves arousal.

WO2007141345 A1 describes a remote monitoring system for neonatal units, to detect and stimulate infant apnea-bradycardia. This application refers to an adjustment of the stimulation energy based on the measured heart rate of the infant.

The initialization of the stimulation parameters is performed from a pre-established database and, therefore, does not take into account some physiological specificities of the patient (weight, gender, etc.), while clinical studies have demonstrated a relationship of the response to the kinesthetic stimulation, according to these physiological parameters.

WO 96/28093 A1 also teaches a system that delivers a stimulus to reduce the frequency or duration of an apnea episode. At the stimulation level, this document simply describes the low and high limits of the stimulation energy that may stop apnea without waking the patient.

WO 2009/154458 A2 teaches a system which detects apnea and in turn causes an inspiration reflex by stimulation in the ear region. Various apnea detection methods are cited, and stimulation may be electrical or mechanical. The stimulation strategy is simple, and involves applying pulse trains as long as the disorder is present. However, the stimulation parameters may vary without indicating rules of variation. A change in stimulation parameters to avoid habituation is also cited.

US 2010/0048985 A1 describes a similar device for applying stimuli by various natures (e.g., audio or ultrasonic stimulation of the ear, eye stimulation, mechanical stirrer, etc.). The device also analyzes respiratory activity to evaluate the effectiveness of the stimulation so that the patient or the physician can change the settings of the generator as desired with different stimuli doses.

Finally, US 2008/009915 A1 discloses a system that detects respiratory disorders using a nasal or other cannula and applies a particular vibratory stimulation in the ear region. The objective is to stop apnea, without waking the patient, by stimulation which may be manually or automatically adjusted, depending on physiological characteristics of the patient or of the sleep cycles. This document also generally cites the optimization of the stimulation parameters to fit the severity of the patient's disorder, without giving details on the stimulation parameters adjustment. A change in parameters to prevent habituation is also cited.

SUMMARY

The present invention provides a system that optimizes the stimulation parameters both in anticipation of forthcoming respiratory disorders and also during an occurrence of a disorder, so as to adjust the stimulation energy to a level appropriate to the disorder and to its possible persistence, while minimizing the risk of waking the patient.

Specifically, an embodiment of the invention discloses a device for treating a breathing disorder in a patient by kinesthetic stimulation, characteristically including:

a processor configured to detect a respiratory disorder,
wherein the processor is further configured to produce kinesthetic stimulation control signals in response to a detection of a respiratory disorder; and
at least one kinesthetic effector adapted to be applied to a patient's external skin site, and including a vibrating electromechanical transducer capable of receiving the control signals and outputting a kinesthetic stimulation energy determined by the control signals;
wherein the processor is further configured to determine the effectiveness of stimulation by detecting a cessation of the respiratory disorder;
wherein the processor is further configured to determine a stimulation energy.

The determination of stimulation energy includes:
selecting a starting energy value and varying the energy value depending on the effectiveness of previous stimulation, the energy value being capped at a maximum value, and
for a first stimulation, selecting an initial value depending on the patient's physiological parameters.

According to various advantageous subsidiary characteristics:
the processor is further configured to provide stimulation following a previous stimulation, to determine the starting energy value based on an effective energy value having stopped the respiratory disorder during a previous stimulation;
the maximum value is a variable value function of at least one factor of the group formed by: gender, age, BMI index, patient's sleep stage, and the type of respiratory disorder which affects the patient;
determining a stimulation energy includes:
incrementally raising the energy level from the starting energy value, as long as the respiratory disorder does not cease;
comparing each incremented energy value to the maximum value;
fixing an energy value greater than the maximum allowable value in a case of a detection of a serious episode of the respiratory disorder;
raising the maximum permissible energy value as a result of exceeding the maximum value during a previous respiratory disorder, without waking the patient; and
selecting the initial energy value from at least an initial table of energy values for various combinations of gender, age, size and weight and/or based on a detected or parameterized type of respiratory disorder.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

Figure 1:
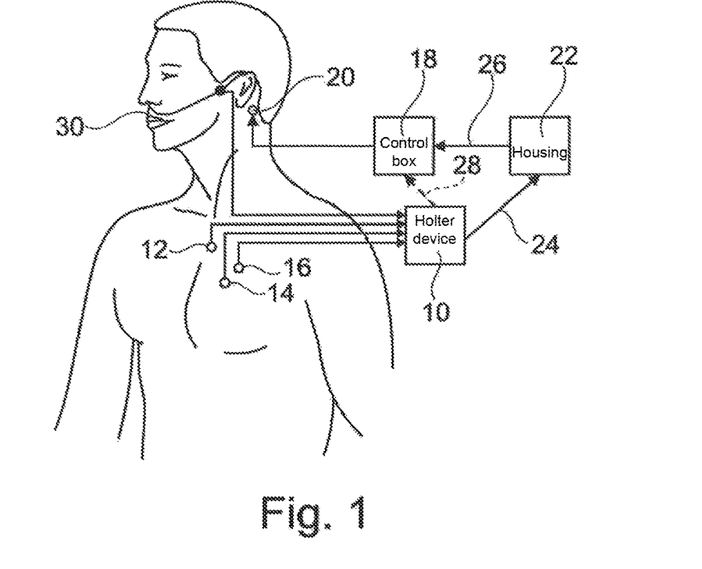
FIG. 1 schematically illustrates a system fitted to a patient according to an embodiment of the invention.

FIG. 1 schematically illustrates the main components of a system used for the implementation of the present disclosure.

The system includes a Holter device 10 connected to various sensors or electrodes 12, 14, 16, for measuring physiological signals such as heart rate, respiration, oxygen saturation, pulse wave, phonocardiogram, etc. In the following, we will focus mainly on the respiratory amplitude or respiratory pressure, which are simple parameters to obtain. However, this measure is not intended to be restrictive and the disclosed systems and methods can be as well implemented from other physiological signals collected from the patient.

The system further includes a kinesthetic stimulation device, with a generator housing 18 producing pulses for control of a stimulation kinesthetic effector 20, consisting, for example, of a vibrator disposed in a sensitive region of the skin, typically (in adults) in the mastoid bone region near the ear. Vibrotactile stimulation applied to the skin by the effector 20 is detected by the sensory receptors or mechanoreceptors of the body, and this information is transmitted through sensory nerves to the autonomous central nervous system.

The effector 20 is, for example, a transducer such as C10-100 of Precision Microdrives or C2 Tactor of Engineering Acoustics. The transducer is of a few grams which can emit vibrations due to an integrated vibrator excited by pulse trains of variable amplitude and length, typically at a frequency of 250 Hz which is the nominal resonance frequency of this particular effector, and which is also the frequency at which the mechanoreceptors of the skin are the most sensitive. However, other types of effectors can also be used effectively.

The control box 18 is controlled by a microcontroller which is configured to adjust the intensity (i.e., the energy) of kinesthetic stimulation by controlled variation of the amplitude, the number, the duration, and/or the frequency of the stimulation pulse trains forming the signal applied to the effector 20.

The system also includes a housing 22 coupled to the Holter device 10 and to the control box 18 by a respective wire or wireless connection 24, 26, to receive data from the Holter device 10, process such data and in response produce information of kinesthetic stimulation control to be transmitted to the control box 18. Alternatively, data processing and control of the control box 18 can be operated within the Holter device 10 and transmitted directly by a link 28 to the housing 18.

Finally, the system is configured to measure the respiratory rate, for example a nasal pressure cannula 30 (and/or an oral cannula) or other type of sensor such as a thermistor or a mechanical sensor of the abdomen and/or the thoracic cavity volume changes (e.g., by a belt equipped with sensors sensitive to stretching). A ventilatory signal is delivered to the Holter device 10 which is continuously analyzed in order to detect in real time the occurrence of an apnea or of a hypopnea.

The system operates as follows: when apnea is detected by the Holter device 10, the control box 18 triggers a kinesthetic stimulus to trigger a response of the autonomic nervous system so that, in response, the autonomic nervous system causes a change in respiration and therefore triggers a respiratory reflex that stops the apnea.

The energy with which the stimulation is performed determines the success of the therapy. If the stimulation energy is too low, it is not effective. If the stimulation energy is too high, there is a risk of waking the patient. If the stimulation energy is too repetitive, a habituation phenomenon can be created, which may in turn reduce the effectiveness of the stimulation.

Furthermore, the same energy may have a different effectiveness depending on the patient, the sleep stage or even the apneic event itself.

The system as described with reference to FIG. 1 is able to optimize the energy of kinesthetic stimulation to alleviate the above problems in real-time. It is understood that to modulate the "energy" of stimulation, the following parameters can be modified: the intensity of vibration stimulation, the frequency of occurrence, the number of pulses or pulse trains, the envelope shape, etc., or any combination of these parameters.

The optimization of the energy is carried out first with an initialization based on patient parameters. The initialization sets the initial stimulation energy.

The efficiency of the same energy delivered under the same conditions (e.g., same episode of apnea, same sleep stage) may change depending on the patient's physical characteristics such as gender, age and body mass index (BMI). Thus, the more the subject is aged, the larger the energy must be to achieve the same effectiveness. Similarly, when the BMI increases, the energy must also be increased.

The system is then able to adapt the energy needed for processing during the night and optionally in the same episode as a function of the effectiveness of the stimulation and of the risk of awakening.

Figure 2:
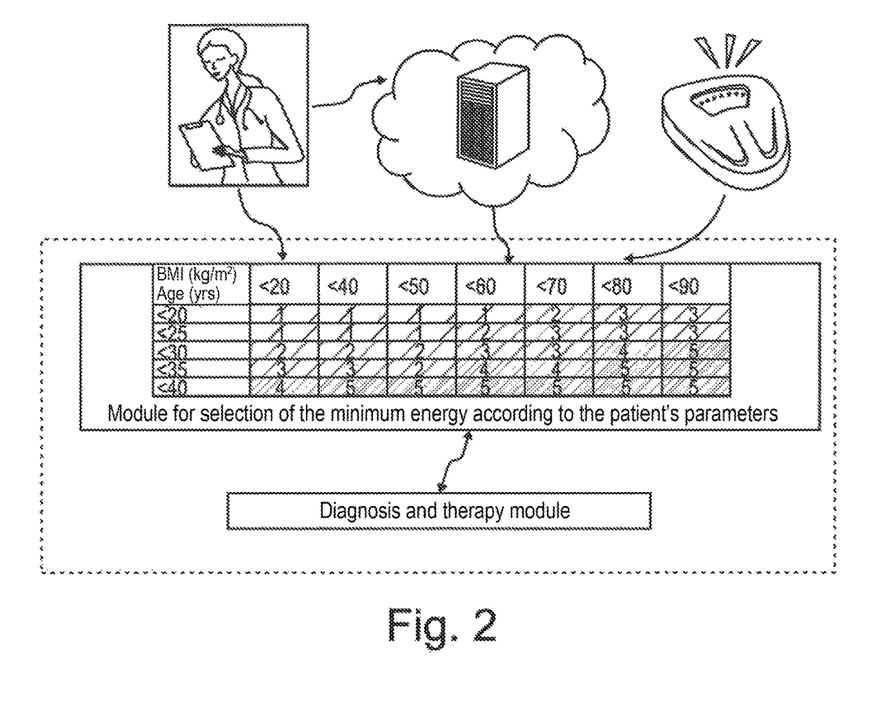
FIG. 2 illustrates an exemplary table of initial stimulation energy values stored in the system.

According to a particular implementation, and with reference to FIG. 2, by default an energy table based on these three parameters (gender, age and BMI—FIG. 2 showing a table for one gender only) is established and stored according to clinical data available in the field. For this purpose, a population of patients with sleep apnea is subject to stimulation during polysomnography with varying stimulation energy, for example randomly varying. The effectiveness of the stimulation is measured and the analysis of the population allows for determining the minimum effective energies based on clinical patients characteristics.

At the initiation of the stimulation system, the data is requested from the user and by default the energy value is then stored as the initial value based on the data.

The ability to update the data is advantageously provided in the case where a significant drop or gain in patient weight occurs which may change the effectiveness of the therapy if the system does not modify the energy accordingly.

FIG. 2 shows, in addition to the value table, the modalities for determining the starting energy. The gender, BMI value and age are entered into the system using a user interface (e.g., touchscreen, keyboard-screen combination, etc.) either directly by the physician on the system during a consultation or, always by the physician, via a network connection, or via the patient himself (e.g., using a scale connected by local network such as Bluetooth to the system).

The system then uses the data table above, stored in its memory, to determine the appropriate starting energy based on these parameters. From this initialization, the system is capable of varying the stimulation energy to maintain efficient energy but without causing the patient to awaken.

Figure 3:
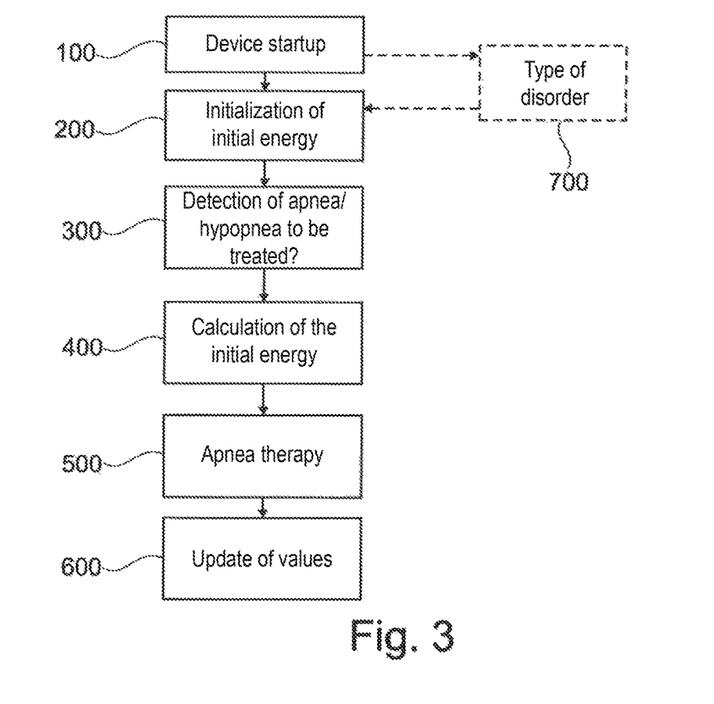
FIG. 3 is a general flowchart of a method for adjusting the stimulation energy implemented by the system.

Thus, referring to FIG. 3, after switching on the apparatus (step 100) the initialization of the stimulation energy value described above is implemented (step 200). When an event to be processed (apnea or hypopnea detection in step 300) occurs, an algorithm executed in the system control unit first determines an energy that will be used at the start of processing (step 400, detailed in FIG. 4C). Then, during the processing phase (step 500, detailed in FIG. 3A), the energy can change depending on the observed efficacy and on an upper limit related to the risk of awakening. After completing the event, the system is able to optimize the energy to be used during the update values phase (step 600, detailed in FIG. 3B).

Details of this method are illustrated in FIGS. 3A to 3D. First referring to FIG. 3A, which details the processing step 500. Once the initial energy has been determined and an apnea or hypopnea has been detected (step 510), the system applies stimulation energy with the initial energy (step 520). If the system detects a breathing disorder has stopped (step 530), the system stores the energy as effective (step 540). Otherwise, the system increases the stimulation energy setpoint by a given increment (step 560) and triggers a new stimulation (return to step 520) with the new energy setpoint and continues the stimulation until the breathing disorder has stopped. Between steps 530 and 560, a step 550 is further provided to limit the stimulation energy applied to an admissible maximum energy, which can be an absolute energy value or can depend on criteria of gender, age, BMI index and possibly other criteria, including the patient's sleep stage (slow-wave sleep I, II, III, IV and REM sleep), the maximum energy being a function of the sleep stage.

Figure 3A:
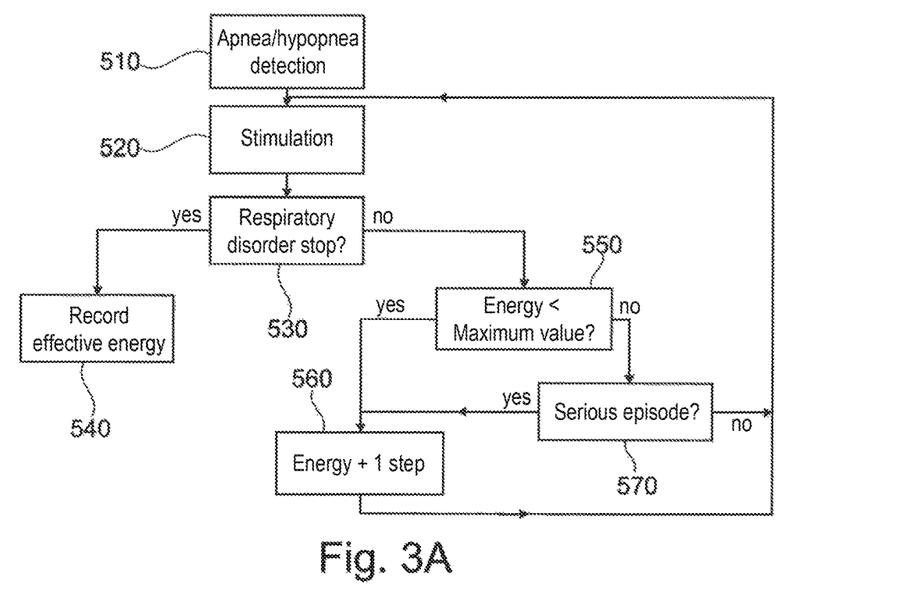
FIGS. 3A-3D illustrate four specific flowcharts associated with the general flow chart of FIG. 3.

Step 550 may be improved by providing that in the case of achieving the maximum allowable energy value, the system identifies, using the different sensors 12, 14, 16 and 30, if the episode of respiratory disorder is a serious episode (e.g., apnea too long, a desaturating episode, etc.) (step 570). If so, the stimulation energy is again increased by one increment (step 560) to exceed the maximum permissible value, and a new stimulation therapy is performed (step 520), to ensure the disappearance of the disorder, but with the risk of waking the patient.

Figure 3B:
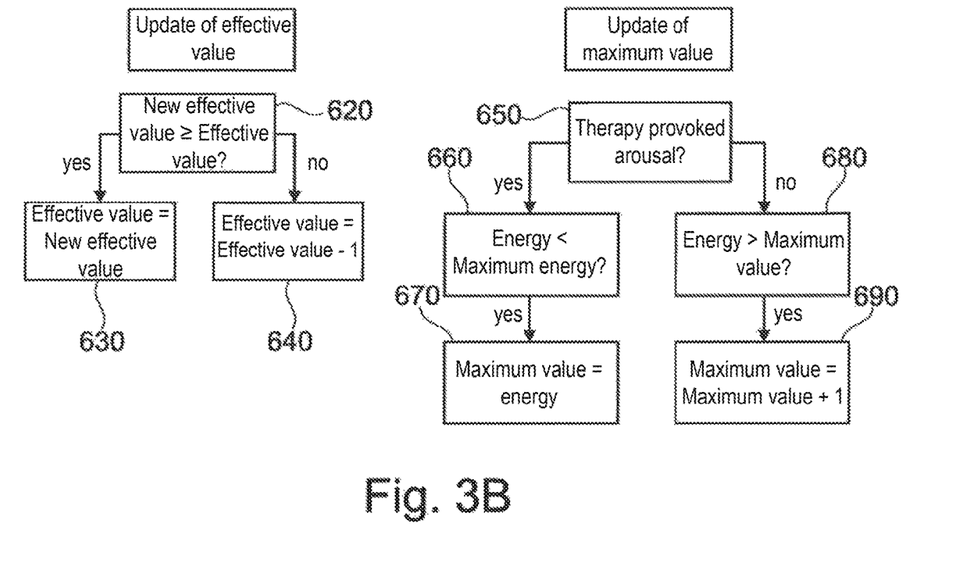

FIG. 3B illustrates in detail the method 600 of updating the two variable energy values, i.e. the value of the energy considered effective to make the disorder disappear and the maximum allowable energy. This update is performed at the end of each therapy.

In step 620, the system determines if the effective energy value was incremented at step 560 during the previous therapy. If so, the starting setpoint energy for the next therapy is determined as the effective energy value after incremention (step 630). If not, the setpoint energy is decreased to prevent upward drift (step 640).

Regarding the maximum permissible value, the system determines if the previous processing stage 500 caused a patient awakening (step 650) and, if so, determines at step 660 if the energy level that caused this awakening is or is not less than the maximum permissible value at the time of therapy. If so, the system has a new fixed maximum permissible energy value that caused the awakening (step 670). The detection of the awakening may vary depending on the application. For example, the detection can be done by simply using an activator actuated by the patient when he wakes. The detection can also be done automatically using an actimetry sensor or through the study of the evolution of ventilation as described in EP 1317943 A1 (Sorin CRM), which is hereby incorporated by reference in its entirety.

If, however, at the test of step 650 it is determined that the previous therapy phase 500 did not cause awakening, the system determines whether the stimulation energy at the end of therapy (thus resulting in the cessation of disorder, without revival) was greater than the current maximum permissible value (step 680). If so, the system sets a new maximum permissible value as a value equal to the previous value increased by a given increment.

It is understood that these two adjustments allow for optimization of the delivered stimulation energy, increasing the chances of reaching a cessation of the disorder episode while minimizing the risk of awakening.

In this example, the optimization is done continuously during the night after each treated episodes. In a simplified version, it is also possible to optimize the delivered energy values only after a whole night, based on the success rate of therapy and the wakeup ratio of the previous night for application for the current night.

Figure 3C:
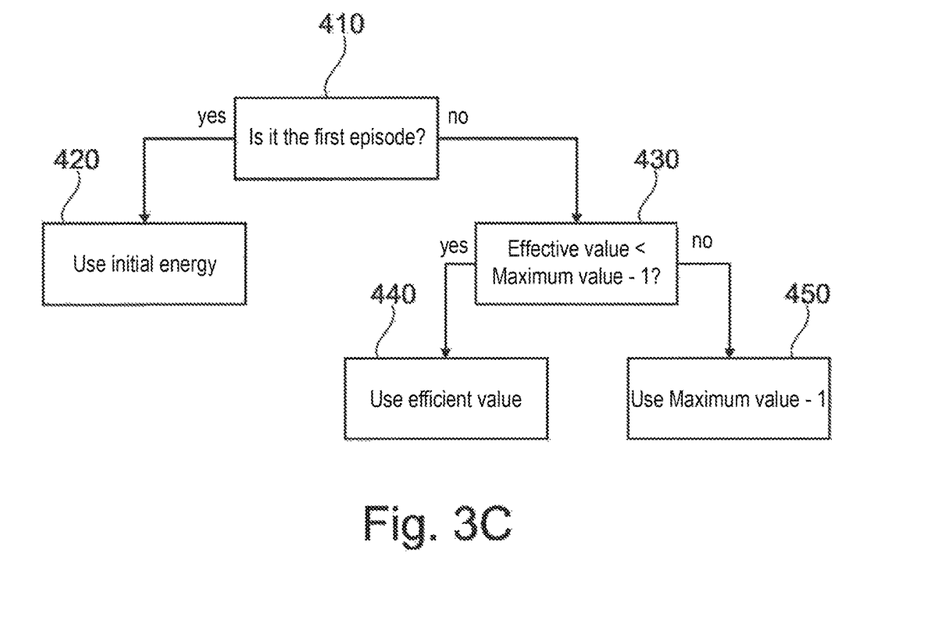

FIG. 3C illustrates step 200 in detail, i.e. the method by which energy is determined during when starting a therapy according to the latest energy used and to the maximum permissible value.

In step 410, the system determines if a sleep disorder episode is the first episode of the night, which can be easily determined using an incremental counting of episodes. If so, the system uses the initially determined energy based on the parameters of gender, age and BMI index (step 420) for the first therapy. If not, the system determines (step 430) if the effective value used in a previous episode is less than the maximum permissible value used for the previous episode. If so, the initial energy value is set as the energy value that was effective in the previous episode (step 440). If not, the system uses as a starting energy value the maximum permissible value used in the previous episode (step 450).

The above description is given as an example for an application considering only one type of respiratory disorder. Depending on the types of respiratory disorders, e.g. apnea, central or obstructive hypopnea, flow rate limiting, etc., it will be understood that the adjustment rules of the stimulation energy may be different. Notably, the first issued energy level will be adjusted. As FIG. 3 shows, an optional step 700 is provided between the steps 100 and 200 and the system determines the type of disorder, independently using the sensors 12, 14 and 16 or by input made by the patient or by a caregiver treating the found type of disorder prior to start-up.

Figure 3D:
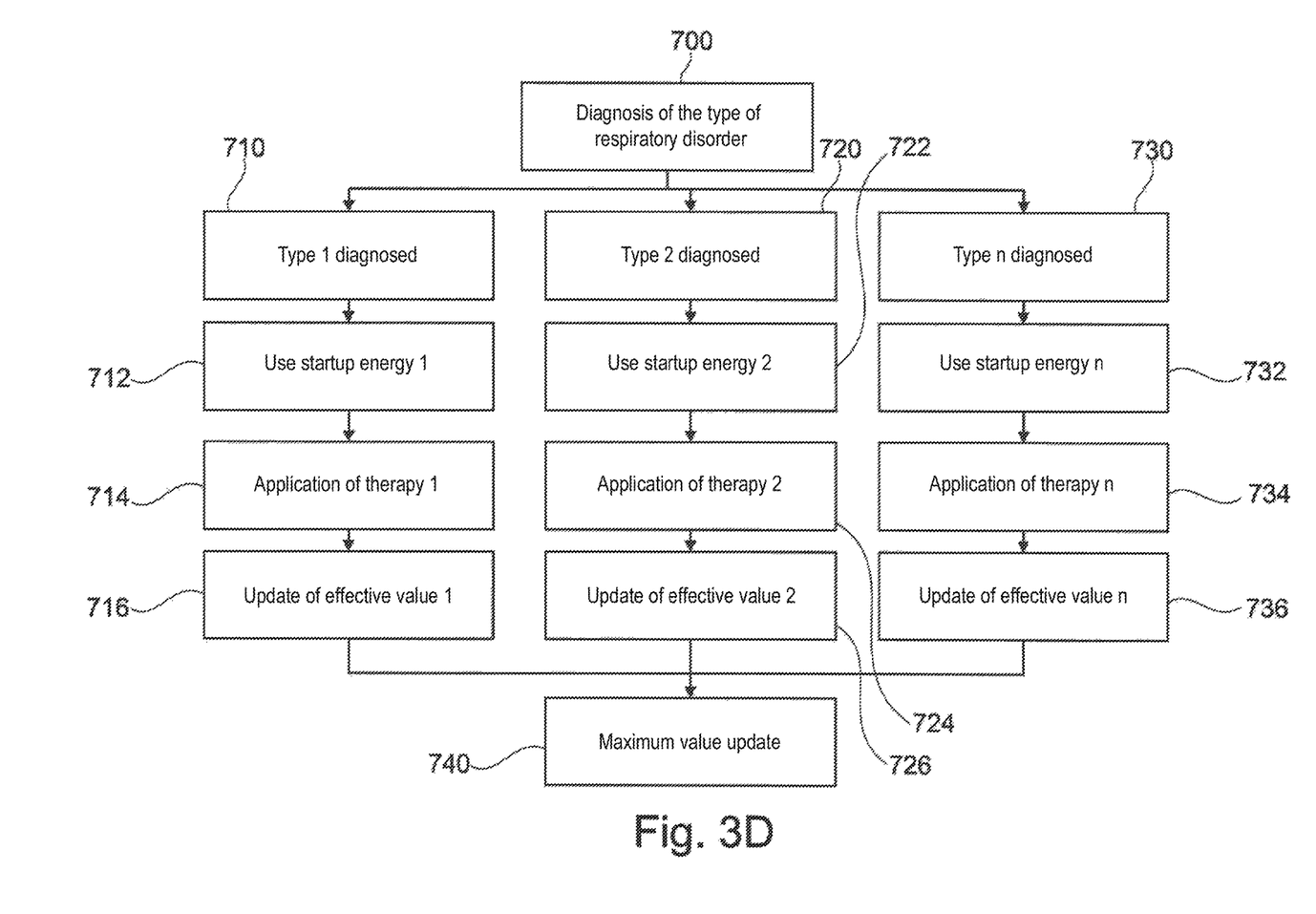

FIG. 3D explains step 700. Three types of disorders can be selectively diagnosed (steps 710, 720, 730). Depending on the type of detected disorder, the system chooses a certain energy of initial stimulation (steps 712, 722, 732), and then applies a kinesthetic therapy as before (steps 714, 724, 734), and updates the values of admissible effective energy as before (steps 716, 726, 736) for each of the types of disorders. The maximum permissible energy value can be commonly chosen for the different types of disorders (step 740).

What is claimed is:

1. An optimization device for treatment of a respiratory disorder of a patient by stimulation, including:
    a processor configured to detect a respiratory disorder episode;
    wherein the processor is further configured to produce kinesthetic stimulation control signals in response to detection of the respiratory disorder episode, wherein the kinesthetic stimulation control signals are associated with a kinesthetic stimulation energy value; and
    at least one effector adapted to receive the stimulation control signals and to deliver the kinesthetic stimulation energy value determined by the kinesthetic stimulation control signals;
    wherein the processor is further configured to determine an effectiveness of the stimulation energy by detecting a cessation of the respiratory disorder episode;
    wherein the processor is further configured to determine the kinesthetic stimulation energy by:
        for a first episode, selecting an initial energy value depending on physiological parameters of the patient, and
        for a subsequent episode, selecting a starting energy value and varying the energy value depending on the effectiveness of stimulation for a previous episode, the energy value being capped at a maximum value,
    wherein the processor is further configured to update the maximum value of the energy value following the subsequent episode such that the energy value remains at a therapeutic level to treat the respiratory disorder while limiting an occurrence of awakenings of the patient.

2. The device of claim 1, wherein the processor is further configured to determine the kinesthetic stimulation energy by, for a subsequent episode, determining the starting energy value based on an effective energy value having actually stopped the respiratory disorder episode during a previous episode.

3. The device of claim 1, wherein the maximum value is based on a variable value function of at least one of the patient's sex, the patient's age, the patient's body mass index (BMI), the patient's sleep stage, or a type of respiratory disorder that affects the patient.

4. The device of claim 1, wherein the processor is further configured to determine the kinesthetic stimulation energy by incrementally raising the energy value from the initial or starting energy value, as long as the respiratory disorder episode does not cease.

5. The device of claim 4, wherein the processor is further configured to determine the kinesthetic stimulation energy by comparing each incrementally raised energy value to the maximum value.

6. The device of claim 5, wherein the processor is further configured to determine the kinesthetic stimulation energy by raising the energy value greater than the maximum value when a severe episode of the respiratory disorder is detected.

7. The device of claim 6, wherein the processor is further configured to set a new value if after raising the energy value greater than the maximum value, the patient is not awakened.

8. The device of claim 1, wherein the processor is further configured to determine the kinesthetic stimulation energy by, for the first episode, selecting the initial energy value from an initial energy value table for different combinations of at least gender, age, height, weight, and a detected or selected type of respiratory disorder.

9. The device of claim 1, wherein the at least one effector comprises at least one kinesthetic effector adapted to be applied to a patient's external skin site and comprising a vibrating electromechanical transducer.

10. The device of claim 1, wherein the first episode is a first episode occurring during a first time period during which the patient is sleeping.

11. The device of claim 10, wherein the time period during which the patient is sleeping is a night during which the patient is sleeping.

12. The device of claim 10, wherein the subsequent episode occurs during a subsequent time period during which the patient is sleeping and the previous episode is an episode that occurred during a previous time period during which the patient was sleeping.

\* \* \* \* \*